(12) United States Patent
Kanai et al.

(10) Patent No.: US 11,789,169 B2
(45) Date of Patent: Oct. 17, 2023

(54) X-RAY DETECTOR

(71) Applicant: CANON MEDICAL SYSTEMS CORPORATION, Otawara (JP)

(72) Inventors: Eri Kanai, Otawara (JP); Hiroaki Miyazaki, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 85 days.

(21) Appl. No.: 17/241,397

(22) Filed: Apr. 27, 2021

(65) Prior Publication Data

US 2021/0356609 A1   Nov. 18, 2021

(30) Foreign Application Priority Data

May 12, 2020   (JP) ................................ 2020-083646

(51) Int. Cl.
| | | |
|---|---|---|
| *G01T 1/29* | (2006.01) | |
| *A61B 6/03* | (2006.01) | |
| *G01T 1/24* | (2006.01) | |

(52) U.S. Cl.
CPC ............ *G01T 1/2971* (2013.01); *A61B 6/032* (2013.01); *G01T 1/247* (2013.01)

(58) Field of Classification Search
CPC ........ G01T 1/2971; G01T 1/247; A61B 6/032
See application file for complete search history.

(56) References Cited

U.S. PATENT DOCUMENTS

| | | | |
|---|---|---|---|
| 4,135,247 A | 1/1979 | Gordon et al. | |
| 6,724,855 B2 | 4/2004 | Sugawara et al. | |
| 7,479,639 B1 | 1/2009 | Shahar et al. | |
| 8,044,362 B2 | 10/2011 | Goo et al. | |
| 9,886,925 B2 | 2/2018 | Wang et al. | |
| 2007/0280409 A1* | 12/2007 | Konno | .................... G01T 1/249 378/19 |
| 2017/0276808 A1* | 9/2017 | Takahashi | ............. G01T 1/2018 |
| 2019/0213759 A1* | 7/2019 | Lee | ........................ G06T 11/003 |

FOREIGN PATENT DOCUMENTS

| | | |
|---|---|---|
| CN | 107076862 A | 8/2017 |
| EP | 3 510 928 A1 | 7/2019 |

OTHER PUBLICATIONS

Extended European Search Report dated Oct. 4, 2021 in European Patent Application No. 21173397.7, 6 pages.
Chinese Office Action dated Jun. 26, 2023, in Chinese Patent Application No. 202110493553.5, 7 pages.
European Office Action dated Jul. 4, 2023, in European Patent Application No. 21 173 397.7, 5 pages.

* cited by examiner

*Primary Examiner* — David P Porta
*Assistant Examiner* — Casey Bryant
(74) *Attorney, Agent, or Firm* — Oblon, McClelland, Maier & Neustadt, L.L.P.

(57) ABSTRACT

An X-ray detector according to embodiments is an X-ray detector of a direct conversion type in which a plurality of X-ray detection elements are arranged in a column direction and a channel direction and voltage is applied between anodes and cathodes. The X-ray detector includes processing circuitry. The processing circuitry performs control so as not to use, for generation of image data, data from the X-ray detection elements in end portions in one of the column direction and the channel direction of the X-ray detection elements, and so as to use, for generation of image data, data from the X-ray detection elements in other than the end portions.

9 Claims, 8 Drawing Sheets

X-RAY DETECTOR

CROSS-REFERENCE TO RELATED APPLICATIONS

This application is based upon and claims the benefit of priority from Japanese Patent Application No. 2020-083646, filed on May 12, 2020; the entire contents of which are incorporated herein by reference.

FIELD

Embodiments described herein relate generally to an X-ray detector.

BACKGROUND

A photon counting detector includes a plurality of X-ray detection elements that are two-dimensionally arranged in a column direction (slice direction) and a channel direction. Here, in some cases, characteristics of X-ray detection elements in both end portions in the column direction may be degraded as compared to X-ray detection elements other than the X-ray detection elements in the both end portions in the column direction. Similarly, in some cases, characteristics of X-ray detection elements in both end portions in the channel direction may be degraded as compared to X-ray detection elements other than the X-ray detection elements in the both end portions in the channel direction.

DETAILED DESCRIPTION

One of problems to be solved by embodiments disclosed in the present specification and drawings is to prevent degradation of characteristics of X-ray detection elements in end portions among a plurality of X-ray detection elements that contribute to generation of image data. However, the problems to be solved by the embodiments disclosed in the present specification and drawings are not limited to the problem as described above. Problems corresponding to effects that are achieved by configurations illustrated in the embodiments described below may be regarded as other problems.

An X-ray detector according to the embodiments is an X-ray detector of a direct conversion type in which a plurality of X-ray detection elements are arranged in a column direction and a channel direction and voltage is applied between anodes and cathodes. The X-ray detector includes a control unit. The control unit performs control so as not to use, for generation of image data, data from X-ray detection elements in end portions in the column direction or the channel direction, and so as to use, for generation of image data, data from X-ray detection elements in portions other than the end portions.

Embodiments of an X-ray detector and an X-ray CT apparatus will be described in detail below with reference to the accompanying drawings. Further, the X-ray detector and the X-ray CT apparatus according to the present application is not limited by the embodiments described below. Furthermore, the embodiments may be combined with other embodiments or conventional techniques within the scope as long as no contradiction is derived. Moreover, in the following description, the same structural elements may be denoted by the same reference symbols, and repeated explanation may be omitted.

Furthermore, the X-ray CT apparatus described in the embodiments below is an apparatus that is able to perform photon counting CT. For example, the X-ray CT apparatus described in the embodiments below is an apparatus that is able to reconstruct X-ray CT image data by counting photons of X-rays (X-ray photons) that have transmitted through a subject by using an X-ray detector (photon counting detector). Moreover, for example, the X-ray detector described in the embodiments below is a detector of a direct conversion type that directly converts X-ray photons into charges that are proportional to energy.

First Embodiment

Figure 1:
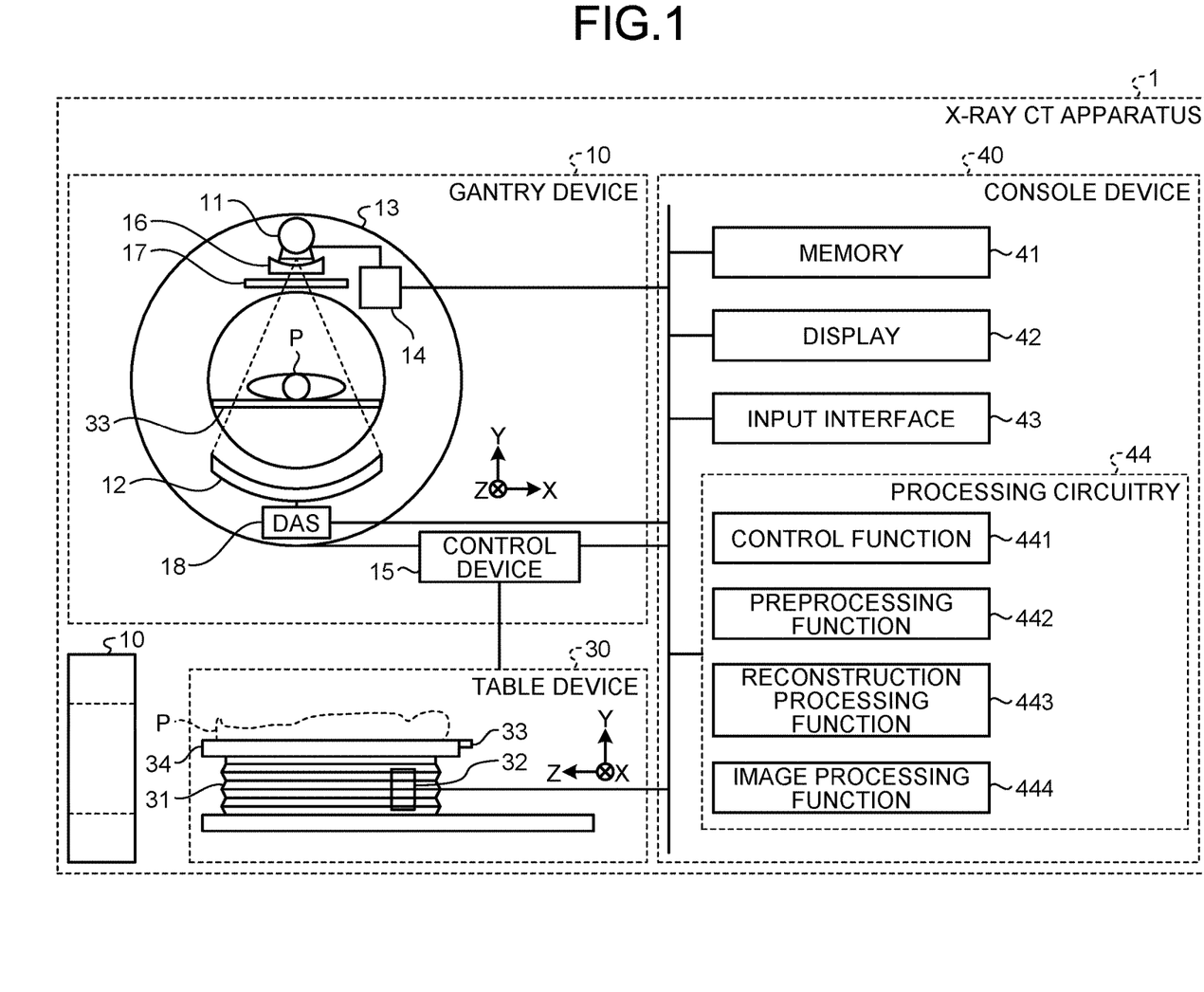
FIG. 1 is a diagram illustrating an example of a configuration of an X-ray CT apparatus according to a first embodiment.

FIG. 1 is a diagram illustrating an example of a configuration of an X-ray CT apparatus according to a first embodiment. As illustrated in FIG. 1, an X-ray CT apparatus 1 according to the first embodiment includes a gantry device 10, a table device 30, and a console device 40.

Here, in FIG. 1, a rotation axis of a rotary frame 13 in a non-tilted state or a longitudinal direction of a tabletop 33 of the table device 30 is referred to as a Z-axis. Further, an axial direction that is orthogonal to the Z-axis direction and parallel to a floor surface is referred to as an X-axis direction. Furthermore, an axial direction that is orthogonal to the Z-axis direction and the X-axis direction and perpendicular to the floor surface is referred to as a Y-axis direction. Meanwhile, FIG. 1 illustrates a case in which the gantry device 10 is viewed in a plurality of directions for the sake of explanation and the X-ray CT apparatus 1 includes the single gantry device 10.

The gantry device 10 includes an X-ray tube 11, an X-ray detector 12, the rotary frame 13, an X-ray high-voltage generator 14, a control device 15, a wedge 16, a collimator 17, and a data acquisition system (DAS) 18.

The X-ray tube 11 is a vacuum tube that includes a cathode (filament) for generating thermo electrons and an anode (target) for generating X-rays upon collision of the thermo electrons. With application of high voltage from the X-ray high-voltage generator 14, the X-ray tube 11 emits thermo electrons from the cathode to the anode and generates X-rays to be applied to a subject P. Examples of the X-ray tube 11 include an X-ray tube of a rotating anode X-ray tube that generates X-rays by emitting thermo electrons to a rotating anode.

The rotary frame 13 is a circular frame that supports the X-ray tube 11 and the X-ray detector 12 in an opposing manner and allows the X-ray tube 11 and the X-ray detector 12 to rotate under the control of the control device 15. For example, the rotary frame 13 is a casting made of aluminum. Meanwhile, the rotary frame 13 may further support the X-ray high-voltage generator 14, the wedge 16, the collimator 17, the DAS 18, and the like in addition to the X-ray tube 11 and the X-ray detector 12. Further, the rotary frame 13 may further support various components that are not illustrated in FIG. 1.

The wedge 16 is a filter for adjusting an amount of X-rays emitted from the X-ray tube 11. Specifically, the wedge 16 is a filter that transmits and attenuates X-rays emitted from the X-ray tube 11 such that a distribution of X-rays to be applied from the X-ray tube 11 to the subject P matches a distribution that is determined in advance. For example, the wedge 16 may be a wedge filter or a bow-tie filter, and is a filter that is obtained by processing aluminum or the like such that a predetermined target angle and a predetermined thickness are obtained.

The collimator 17 is a lead plate or the like for narrowing down an irradiation range of X-rays that have transmitted through the wedge 16, and a slit is formed by a combination of a plurality of lead plates or the like. Meanwhile, the collimator 17 may also be referred to as an X-ray diaphragm. Further, in FIG. 1, a case is illustrated in which the wedge 16 is arranged between the X-ray tube 11 and the collimator 17, but the collimator 17 may be arranged between the X-ray tube 11 and the wedge 16. In this case, the wedge 16 transmits and attenuates X-rays, which are emitted from the X-ray tube 11 and for which the irradiation range is limited by the collimator 17.

The X-ray high-voltage generator 14 includes a high-voltage generator that includes electrical circuits, such as a transformer (Xformer) and a rectifier, and that generates high voltage to be applied to the X-ray tube 11, and an X-ray control device that controls output voltage corresponding to X-rays generated by the X-ray tube 11. The high-voltage generator may be of a transformer type or an inverter type. Meanwhile, the X-ray high-voltage generator 14 may be arranged on the rotary frame 13 or may be arranged on a fixed frame (not illustrated).

The control device 15 includes processing circuitry including a central processing unit (CPU) or the like, and a driving mechanism, such as a motor and an actuator. The control device 15 receives an input signal from an input interface 43, and controls operation of the gantry device 10 and the table device 30. For example, the control device 15 controls rotation of the rotary frame 13, tilt of the gantry device 10, operation of the table device 30 and the tabletop 33, and the like. As one example, as control of tilting the gantry device 10, the control device 15 rotates the rotary frame 13 about an axis that is parallel to the X-axis direction in accordance with inclination angle (tilt angle) information that has been input. Meanwhile, the control device 15 may be arranged in the gantry device 10, or may be arranged in the console device 40.

The X-ray detector 12 is a photon counting detector, and at every incidence of an X-ray photon as a photon derived from an X-ray that is emitted by the X-ray tube 11 and that has transmitted through the subject P, the X-ray detector 12 outputs a signal by which an energy value of the X-ray photon is measurable. The X-ray photon is, for example, a photon of an X-ray that is emitted by the X-ray tube 11 and that has transmitted through the subject P. The X-ray detector 12 includes a plurality of X-ray detection elements, each of which outputs a 1-pulse electrical signal (analog signal) at every incidence of an X-ray photon. By counting the number of the electrical signals (pulses), it is possible to count the number of X-ray photons that have entered each of the X-ray detection elements. Further, by performing an arithmetic process on the signal, it is possible to measure an energy value of the X-ray photon by which the signal is output. For example, the X-ray detector 12 is a plane detector in which X-ray detection elements are arranged in N columns in the channel direction and in M rows in the slice direction. Meanwhile, for example, the channel direction is a circumferential direction about the X-ray tube 11. Further, for example, the slice direction is a direction along the Z-axis direction as described above, that is, a direction parallel to the Z-axis direction. The slice direction may also be referred to as a column direction or a row direction.

The X-ray detection element is, for example, a semiconductor element (semiconductor detection element) that is made of cadmium telluride (CdTe), cadmium zinc telluride (CdZnTe), or the like, and that includes an anode electrode and a cathode electrode. That is, the X-ray detector 12 according to the present embodiment is a detector of a direct conversion type that directly converts an incident X-ray photon into an electrical signal.

The X-ray detector 12 includes a plurality of X-ray detection elements and a plurality of application specific integrated circuits (ASICs) as read circuits that are connected to the X-ray detection elements and count X-ray photons detected by the X-ray detection elements. The ASIC discriminates individual charges that are output by the X-ray detection element, and counts the number of X-ray photons that have entered the detection element. Further, the ASIC performs an arithmetic process based on magnitudes of the individual charges, and measure energy of the counted X-ray photons. Furthermore, the ASIC outputs a counting result of the X-ray photons as digital data to the DAS 18.

Figure 2:
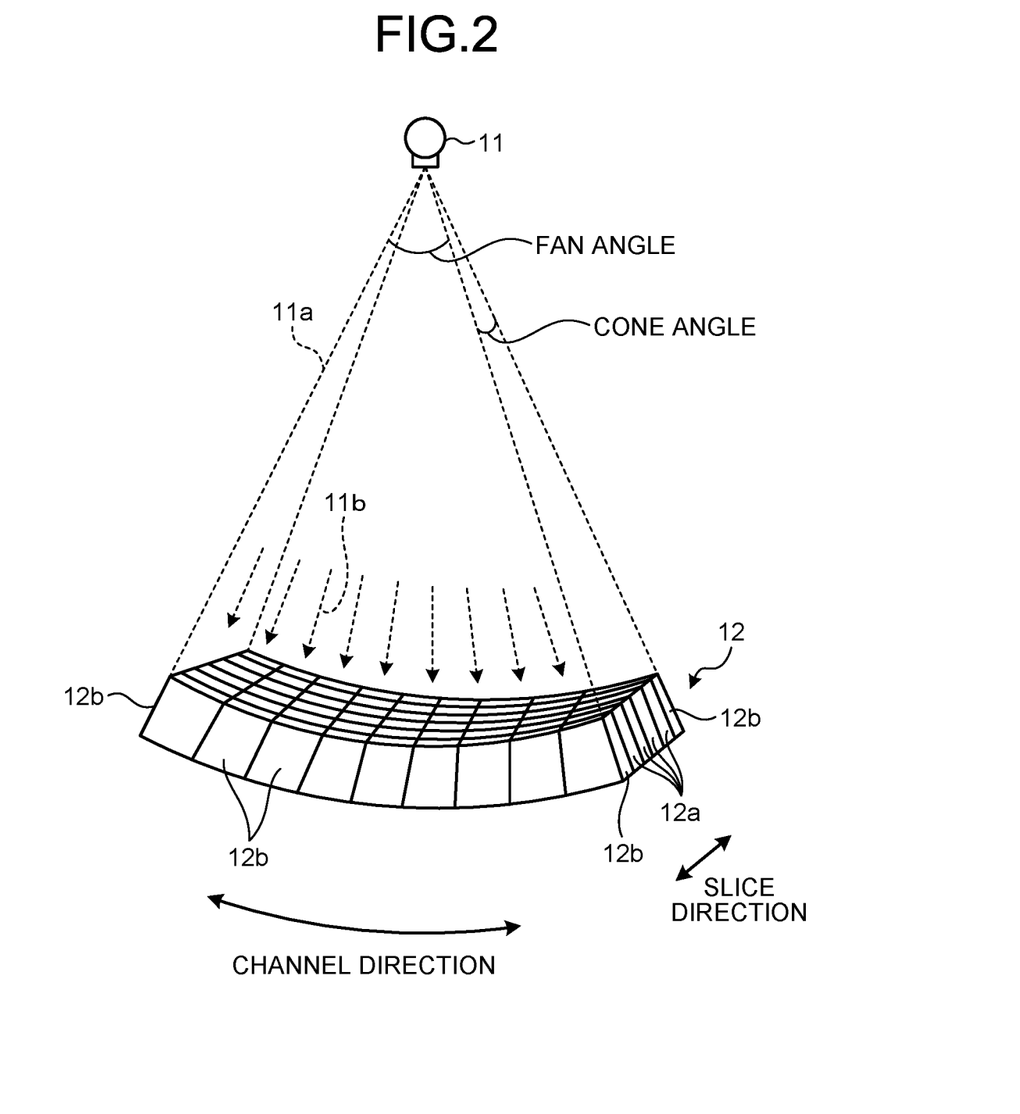
FIG. 2 is a diagram illustrating an example of a configuration of an X-ray detector according to the first embodiment.

FIG. 2 is a diagram illustrating an example of a configuration of the X-ray detector according to the first embodiment. For example, as illustrated in FIG. 2, the X-ray detector 12 includes a plurality of X-ray detector modules 12a and a plurality of X-ray detector modules 12b. Meanwhile, in FIG. 2, an irradiation range of X-rays is indicated by dashed lines 11a, and irradiation directions of the X-rays are indicated by dashed-line arrows lib. As illustrated in FIG. 2, X-rays are emitted in a spread manner at a predetermined fan angle and with a predetermined cone. Meanwhile, a degree of the fan angle (fan angle) is an angle along the channel direction, and a degree of a cone angle (cone angle) is an angle along the slice direction.

The plurality of X-ray detector modules 12a and 12b are arranged in a two-dimensional manner along the slice direction and the channel direction. For example, the plurality of X-ray detector modules 12b are arranged along the channel direction in both end portions in the slice direction. In the example in FIG. 2, the nine X-ray detector modules 12b are arranged along the channel direction in one end portion in the slice direction, and the nine X-ray detector modules 12b are arranged along the channel direction in the other end portion in the slice direction.

Further, a plurality of columns, each of which includes the plurality of X-ray detector modules 12a that are arranged along the channel direction, are arranged along the slice direction between the X-ray detector modules 12b that are arranged in one end portion and the X-ray detector modules 12*b* that are arranged in the other end portion. In the example in FIG. 2, four columns, each of which includes the nine X-ray detector modules 12*a* that are arranged along the channel direction, are arranged along the slice direction. Details of the X-ray detector modules 12*a* and 12*b* will be described later.

Referring back to FIG. 1, the DAS 18 generates detection data on the basis of results of a counting process input from the X-ray detector 12. The detection data is, for example, sinogram. The sinogram is data in which a result of a counting process of counting the number of times of incidence on each of the X-ray detection elements is arranged at each of positions in the X-ray tube 11. The sinogram is data in which the results of the counting process are arranged in a two-dimensional orthogonal coordinate system with axes in a view direction and the channel direction. The DAS 18 generates the sinogram for each of the columns in the slice direction in the X-ray detector 12, for example. Here, the result of the counting process is data in which the number of X-ray photons for each of energy bins is assigned. The DAS 18 transfers the generated detection data to the console device 40. The DAS 18 is implemented by, for example, a processor.

The data generated by the DAS 18 is transmitted, by optical communication, from a transmitter that is arranged on the rotary frame 13 and that includes a light emitting diode (LED) to a receiver that is arranged in a non-rotating portion (for example, a fixed frame or the like, illustration of which is omitted in FIG. 1) of the gantry device 10 and that includes a photodiode, and the data is further transferred to the console device 40. Here, the non-rotating portion is, for example, a fixed frame of the like that supports the rotary frame 13 such that the rotary frame 13 is rotatable. Meanwhile, a method of transmitting the data from the rotary frame 13 to the non-rotating portion of the gantry device 10 is not limited to the optical communication, but it may be possible to adopt any non-contact type data transmission method and a contact type data transmission method.

The table device 30 is a device for placing and moving the subject P as an imaging target, and includes a pedestal 31, a table driving device 32, the tabletop 33, and a support frame 34. The pedestal 31 is a casing that supports the support frame 34 such that the support frame 34 is movable in a vertical direction. The table driving device 32 is a driving mechanism that moves the tabletop 33, on which the subject P is placed, in a long-axis direction of the tabletop 33, and includes a motor, an actuator, and the like. The tabletop 33 that is arranged on an upper surface of the support frame 34 is a board on which the subject P is placed. Meanwhile, the table driving device 32 may move the support frame 34 in the long axis direction of the tabletop 33, in addition to moving the tabletop 33.

The console device 40 includes a memory 41, a display 42, the input interface 43, and processing circuitry 44. Meanwhile, the console device 40 is explained as a component that is separated from the gantry device 10, but the gantry device 10 may include the console device 40 or a part of the structural elements of the console device 40.

The memory 41 is implemented by, for example, a semiconductor memory element, such as a random access memory (RAM) or a flash memory, a hard disk, an optical disk, or the like. The memory 41 stores therein, for example, projection data or CT image data. Further, for example, the memory 41 stores therein a program for causing circuits included in the X-ray CT apparatus 1 to implement various functions. The memory 41 may be implemented by a server group (cloud) that is connected to the X-ray CT apparatus 1 via a network.

The display 42 displays various kinds of information. For example, the display 42 displays various images generated by the processing circuitry 44 or displays a graphical user interface for receiving various kinds of operation from an operator. For example, the display 42 may be a liquid crystal display or a cathode ray tube (CRT) display. The display 42 may be a desktop type or may be configured as a tablet terminal or the like that is able to perform wireless communication with a main body of the console device 40. Further, the display 42 is one example of a display unit.

The input interface 43 receives various kinds of input operation from the operator, converts the received input operation into an electrical signal, and outputs the electrical signal to the processing circuitry 44. Further, for example, the input interface 43 receives input operation on a scan condition, a reconstruction condition for reconstructing CT image data, an image processing condition for generating a post-processed image from the CT image data, and the like from the operator.

For example, the input interface 43 is implemented by a mouse, a keyboard, a trackball, a switch, a button, a joystick, a touchpad for performing input operation by touching an operation surface, a touch screen in which a display screen and a touchpad are integrated, a non-contact input circuit using an optical sensor, a voice input circuit, or the like. Meanwhile, the input interface 43 may be arranged in the gantry device 10. Further, the input interface 43 may be configured with a tablet terminal or the like that is able to perform wireless communication with the main body of the console device 40. Furthermore, the input interface 43 is not limited to those including physical operational components, such as a mouse and a keyboard. For example, examples of the input interface 43 include an electrical signal processing circuitry that receives an electrical signal corresponding to input operation from an external input device that is arranged separately from the console device 40, and outputs the electrical signal to the processing circuitry 44.

The processing circuitry 44 controls the entire operation of the X-ray CT apparatus 1. For example, the processing circuitry 44 executes a control function 441, a preprocessing function 442, a reconstruction processing function 443, and an image processing function 444. Here, for example, processing functions that are implemented by the control function 441, the preprocessing function 442, the reconstruction processing function 443, and the image processing function 444 as the structure elements of the processing circuitry 44 illustrated in FIG. 1 are stored in the memory 41 in a computer-executable program format. The processing circuitry 44 is, for example, a processor that reads each of programs from the memory 41, executes the programs, and implements functions corresponding to each of the read programs. In other words, the processing circuitry 44 that has read each of the programs has each of the functions as illustrated in the processing circuitry 44 in FIG. 1.

Meanwhile, in FIG. 1, all of the processing functions of the control function 441, the preprocessing function 442, the reconstruction processing function 443, and the image processing function 444 are implemented by the single processing circuitry 44, but embodiments are not limited to this example. For example, the processing circuitry 44 may be configured with a combination of a plurality of independent processors, and each of the processors may execute each of the programs and implement each of the processing functions. Furthermore, each of the processing functions included in the processing circuitry 44 may be implemented by being distributed to or integrated in a single or a plurality of processing circuitries.

The control function 441 controls various processes on the basis of input operation that is received from the operator via the input interface 43. Specifically, the control function 441 controls CT scan performed by the gantry device 10. For example, the control function 441 controls operation of the X-ray high-voltage generator 14, the X-ray detector 12, the control device 15, the DAS 18, and the table driving device 32 and controls a process of collecting counting results in the gantry device 10. As one example, the control function 441 controls a process of collecting projection data in a positioning scan for collecting positioning images (scanogram images), and a process of collecting projection data in image capturing (real scan) for collecting images to be used for diagnosis.

Furthermore, the control function 441 causes the display 42 to display images based on various kinds of image data stored in the memory 41, or the like.

The preprocessing function 442 performs pre-processing, such as a logarithmic transformation process, an offset correction process, an inter-channel sensitivity correction process, beam hardening correction, scattered radiation correction, and dark count correction, on the detection data that is output from the DAS 18, and generates projection data.

The reconstruction processing function 443 performs a reconstruction process on the projection data generated by the preprocessing function 442 by using a filtered back projection method, a successive approximation reconstruction method, or the like, and generates CT image data. The reconstruction processing function 443 stores the reconstructed CT image data in the memory 41.

Here, the projection data that is generated from the counting results obtained through the photon counting CT includes information on energy of X-rays that have been attenuated by transmitting through the subject P. Therefore, the reconstruction processing function 443 is able to reconstruct CT image data of a specific energy component, for example. Furthermore, the reconstruction processing function 443 is able to reconstruct CT image data of each of energy components, for example.

Moreover, the reconstruction processing function 443 is able to, for example, assign, to each of pixels of CT image data of each of the energy components, a color tone corresponding to the energy component, and generate image data in which the pieces of CT image data that are color coded in accordance with the energy components are superimposed. Furthermore, for example, the reconstruction processing function 443 is able to generate, by using K-absorption edge specific to a substance, image data by which the substance can be identified. Examples of other image data generated by the reconstruction processing function 443 include monochrome X-ray image data, density image data, and effective atomic number image data.

When the CT image data is to be reconstructed, projection data corresponding to an entire circumference of a subject, i.e., 360 degrees, is needed, and even with use of a half-scan method, projection data corresponding to a fan angle of 180 degrees is needed. Any of the reconstruction methods may be applied to the present embodiment.

The image processing function 444 converts, by using a well-known method, the CT image data generated by the reconstruction processing function 443 to image data of a cross-sectional image of an arbitrary cross section, a three-dimensional image based on a rendering process, or the like, on the basis of the input operation that is received from the operator via the input interface 43. The image processing function 444 stores the converted image data in the memory 41.

Figure 3:
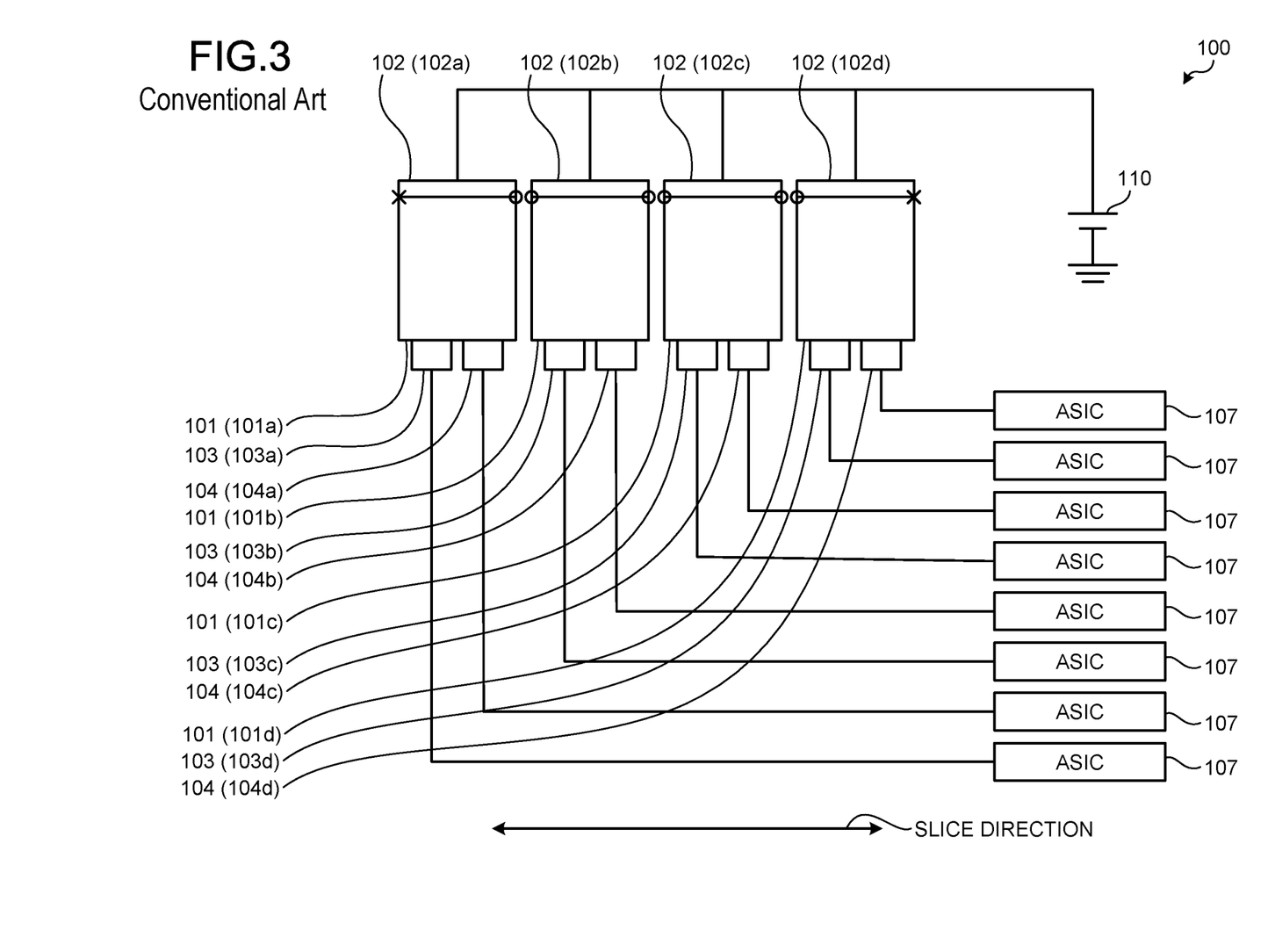
FIG. 3 is a diagram illustrating an example of a conventional configuration of a direct conversion type X-ray detector according to a comparative example.

Thus, the configuration of the X-ray CT apparatus 1 according to the first embodiment has been described above. Here, with reference to FIG. 3, an X-ray detector of an X-ray CT apparatus according to a comparative example will be described. FIG. 3 is a diagram illustrating an example of a configuration of the X-ray detector according to the comparative example. Meanwhile, an X-ray detector 100 according to the comparative example is a detector of a direct conversion type.

As illustrated in FIG. 3, the X-ray detector 100 according to the comparative example includes a plurality of X-ray modules, each of which includes a semiconductor element 101, a cathode (cathode electrode) 102, anodes (anode electrodes) 103 and 104, and an ASIC 107. In the example in FIG. 3, four X-ray detector modules are arranged along the slice direction.

In the following description, when the four semiconductor elements 101 are explained in a distinguished manner, the four semiconductor elements 101 will be referred to as semiconductor elements 101a to 101d. Further, when the four cathodes 102 are explained in a distinguished manner, the four cathodes 102 will be referred to as cathodes 102a to 102d. Furthermore, when the four anodes 103 are explained in a distinguished manner, the four anodes 103 will be referred to as anodes 103a to 103d. Moreover, when the four anodes 104 are explained in a distinguished manner, the four anodes 104 will be referred to as anodes 104a to 104d.

In the example in FIG. 3, in the single X-ray detector module, a single X-ray detection element includes, for example, the semiconductor element 101, the cathode 102, and the anode 103. Furthermore, the single X-ray detection element includes, for example, the semiconductor element 101, the cathode 102, and the anode 104. A single X-ray detection element may correspond to a single pixel, or a plurality of X-ray detection elements may correspond to a single pixel. In the following description, a case will be described in which the single X-ray detection element corresponds to the single pixel.

The cathode 102 is connected to a power source 110. Therefore, bias voltage is applied to the single X-ray detector module by the power source 110. In this manner, by adding (applying) the bias voltage to the X-ray detection element, the X-ray detection element enters a certain state in which it is possible to output a 1-pulse electrical signal at every incidence of an X-ray photon. Further, with application of the bias voltage, the X-ray detector module generates an electric field.

The ASIC 107 is connected to the X-ray detection element. Specifically, the ASIC 107 is connected to the anode 103 or the anode 104. The ASIC 107 discriminates individual charges that is output by the X-ray detection element, and counts the number of X-ray photons that have entered the detection element. Further, the ASIC 107 performs an arithmetic process based on magnitudes of the individual charges, and measure energy of the counted X-ray photons. Furthermore, the ASIC 107 outputs a counting result of the X-ray photons, as digital data, to a DAS (not illustrated).

Here, in FIG. 3, symbols "x" represent two pixels in both end portions in the slice direction, and symbols "○" represent six pixels other than the pixels in the both end portions in the slice direction. Specifically, the pixel represented by the first symbol "x" is a pixel corresponding to the X-ray detection element that includes the semiconductor element 101a, the cathode 102a, and the anode 103a. The pixel represented by the second symbol "x" is a pixel corresponding to the X-ray detection element that includes the semiconductor element 101*d*, the cathode 102*d*, and the anode 104*d*.

Further, the pixel represented by the first symbol "○" is a pixel corresponding to the X-ray detection element that includes the semiconductor element 101*a*, the cathode 102*a*, and the anode 104*a*. The pixel represented by the second symbol "○" is a pixel corresponding to the X-ray detection element that includes the semiconductor element 101*b*, the cathode 102*b*, and the anode 103*b*. The pixel represented by the third symbol "○" is a pixel corresponding to the X-ray detection element that includes the semiconductor element 101*b*, the cathode 102*b*, and the anode 104*b*. The pixel represented by the fourth symbol "○" is a pixel corresponding to the X-ray detection element that includes the semiconductor element 101*c*, the cathode 102*c*, and the anode 103*c*. The pixel represented by the fifth symbol "○" is a pixel corresponding to the X-ray detection element that includes the semiconductor element 101*c*, the cathode 102*c*, and the anode 104*c*. The pixel represented by the sixth symbol "○" is a pixel corresponding to the X-ray detection element that includes the semiconductor element 101*d*, the cathode 102*d*, and the anode 103*d*.

Here, in some cases, characteristics of the pixels represented by the symbols "x" may be degraded as compared to characteristics of the pixels represented by the symbols "○". The reason for this will be described below. For example, in FIG. 3, a distribution of an electric field (electric field distribution) that is generated by the X-ray detection element including the anode 104*a* is affected by an electric field that is generated in the X-ray detector module (the X-ray detector module including the semiconductor element 101*b*) adjacent to the subject X-ray detection element on the right side in FIG. 3. Further, a distribution of the electric field that is generated by the X-ray detection element including the anode 103*b* is affected by the electric field that is generated in the X-ray detector module (the X-ray detector module including the semiconductor element 101*a*) adjacent to the subject X-ray detection element on the left side in FIG. 3.

Furthermore, a distribution of an electric field that is generated by the X-ray detection element including the anode 104*b* is affected by an electric field that is generated in the X-ray detector module (the X-ray detector module including the semiconductor element 101*c*) adjacent to the subject X-ray detection element on the right side in FIG. 3. Moreover, a distribution of the electric field that is generated by the X-ray detection element including the anode 103*c* is affected by the electric field that is generated in the X-ray detector module (the X-ray detector module including the semiconductor element 101*b*) adjacent to the subject X-ray detection element on the left side in FIG. 3.

Furthermore, a distribution of an electric field that is generated by the X-ray detection element including the anode 104*c* is affected by an electric field that is generated in the X-ray detector module (the X-ray detector module including the semiconductor element 101*d*) adjacent to the subject X-ray detection element on the right side in FIG. 3. Moreover, a distribution of an electric field that is generated by the X-ray detection element including the anode 103*d* is affected by the electric field that is generated in the X-ray detector module (the X-ray detector module including the semiconductor element 101*c*) adjacent to the subject X-ray detection element on the left side in FIG. 3.

Furthermore, the same voltage or substantially the same voltage is applied, by the common power source 110, to the four X-ray detector modules illustrated in FIG. 3. Therefore, the distributions of the electric fields generated by the six X-ray detection elements corresponding to the six pixels represented by the symbols "○" are the same or substantially the same.

In contrast, an X-ray detector module is not provided on the left side of the X-ray detection element including the anode 103*a* in FIG. 3. Therefore, a distribution of an electric field that is generated by the X-ray detection element including the anode 103*a* is less likely to be affected by the electric fields that are generated by the X-ray detector modules other than the X-ray detector module including the subject X-ray detection element.

Similarly, an X-ray detector module is not provided on the right side of the X-ray detection element including the anode 104*d* in FIG. 3. Therefore, a distribution of an electric field that is generated by the X-ray detection element including the anode 104*d* is less likely to be affected by the electric fields that are generated by the X-ray detector modules other than the X-ray detector module including the subject X-ray detection element.

Thus, the distributions of the electric fields generated in the six X-ray detection elements corresponding to the six pixels represented by the symbols "○" are different from the distributions of the electric fields generated in the two X-ray detection elements corresponding to the pixels represented by the symbols "x" in the both end portions. Therefore, in some cases, the characteristics of the pixels represented by the symbols "x" may be degraded as compared to the characteristics of the pixels represented by the symbols "○".

To cope with this, in the first embodiment, the X-ray detector 12 is configured as described below in order to prevent degradation of the characteristics of the pixels located in the end portions in the slice direction among the plurality of pixels (or the X-ray detection elements corresponding to the pixels) that contribute to generation of image data.

Figure 4:
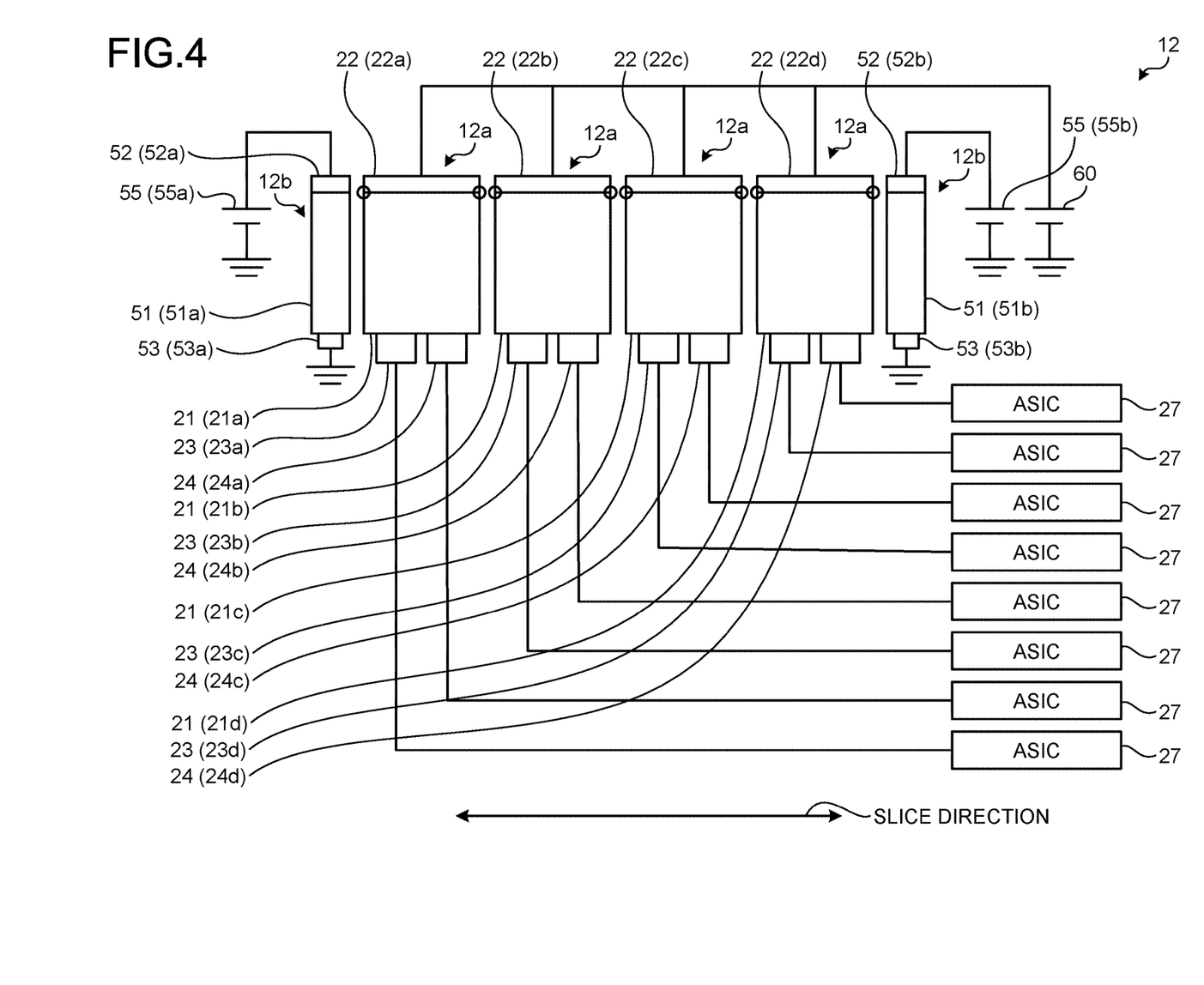
FIG. 4 is a diagram illustrating an example of the configuration of the X-ray detector according to the first embodiment.

Here, the X-ray detector of the X-ray CT apparatus according to the first embodiment will be described with reference to FIG. 4. FIG. 4 is a diagram illustrating an example of a configuration of the X-ray detector according to the first embodiment.

As illustrated in FIG. 4, the X-ray detector 12 according to the first embodiment includes the plurality of X-ray detector modules 12*a*, each of which includes a semiconductor element 21, a cathode 22, anodes 23 and 24, and an ASIC 27. In the example in FIG. 4, the four X-ray detector modules 12*a* are arranged along the slice direction.

Further, the X-ray detector 12 includes the plurality of X-ray detector modules 12*b*, each of which includes a semiconductor element 51, a cathode 52, and an anode 53. In the example in FIG. 4, the X-ray detector modules 12*b* are arranged in both end portions in the slice direction.

In the following description, when the four semiconductor elements 21 are explained in a distinguished manner, the four semiconductor elements 21 will be referred to as semiconductor elements 21*a* to 21*d*. Further, when the four cathodes 22 are explained in a distinguished manner, the four cathodes 22 will be referred to as cathodes 22*a* to 22*d*. Furthermore, when the four anodes 23 are explained in a distinguished manner, the four anodes 23 will be referred to as anodes 23*a* to 23*d*. Moreover, when the four anodes 24 are explained in a distinguished manner, the four anodes 24 will be referred to as anodes 24*a* to 24*d*.

Furthermore, when the two semiconductor elements 51 are explained in a distinguished manner, the two semiconductor elements 51 will be referred to as semiconductor elements 51*a* and 51*b*. Moreover, when the two cathodes 52 are explained in a distinguished manner, the two cathodes 52 will be referred to as cathodes 52a and 52b. Furthermore, when the two anodes 53 are explained in a distinguished manner, the two anodes 53 will be referred to as anodes 53a and 53b.

In the example in FIG. 4, in the single X-ray detector module 12a, a single X-ray detection element includes, for example, the semiconductor element 21, the cathode 22, and the anode 23. Further, the single X-ray detection element includes, for example, the semiconductor element 21, the cathode 22, and the anode 24. A single X-ray detection element may correspond to a single pixel, or a plurality of X-ray detection elements may correspond to a single pixel. In the following description, a case will be described in which the single X-ray detection element corresponds to the single pixel.

The cathode 22 is connected to a power source 60. The power source 60 applies bias voltage to the X-ray detector module 12a. More specifically, the power source 60 applies bias voltage between the cathode 22 and the anodes 23, 24. By applying the bias voltage to the X-ray detection element, the X-ray detection element enters a certain state in which it is possible to output a 1-pulse electrical signal at every incidence of an X-ray photon. The bias voltage is one example of voltage.

The ASIC 27 is connected to the X-ray detection element. Specifically, the ASIC 27 is connected to the anode 23 or the anode 24. The ASIC 27 discriminates individual charges that are output by the X-ray detection element, and counts the number of X-ray photons that have entered the detection element. Further, the ASIC 27 performs an arithmetic process based on magnitudes of the individual charges, and measure energy of the counted X-ray photons. Furthermore, the ASIC 27 outputs a counting result of the X-ray photons, as digital data, to the DAS 18.

Furthermore, in the example in FIG. 4, in the single X-ray detector module 12b, a single X-ray detection element includes, for example, the semiconductor element 51, the cathode 52, and the anode 53. In the following description, a case will be described in which a single X-ray detection element corresponds to a single pixel. Meanwhile, the X-ray detector module 12b may include a plurality of X-ray detection elements. In this case, the plurality of X-ray detection elements may correspond to a single pixel. A size of the X-ray detector module 12b may be the same as or different from a size of the X-ray detector module 12a.

The cathode 52 is connected to a power source 55. The power source 55 applies bias voltage to the X-ray detector module 12b. More specifically, the power source 55 applies bias voltage between the cathode 52 and the anode 53. By applying the bias voltage to the X-ray detection element, the X-ray detection element enters a certain state in which it is possible to output a 1-pulse electrical signal at every incidence of an X-ray photon. In the following, when the two power sources 55 are explained in a distinguished manner, the two power sources 55 will be referred to as power sources 55a and 55b.

Here, the anode 53 according to the first embodiment is grounded and an ASIC (for example, the ASIC 27) that is a read circuit is not connected to the anode 53 of the X-ray detector module 12b. Therefore, a signal from the X-ray detector module 12b is not used for generation of image data. Therefore, the X-ray detector module 12b may also be referred to as a dummy detector module. In the first embodiment, the X-ray detector module 12b does not contribute to generation of image data. Further, with application of the bias voltage, the X-ray detector module 12b generates an electric field and prevents degradation of characteristics of a specific X-ray detection element.

In FIG. 4, symbols "○" represent eight pixels other than pixels in both end portions in the slice direction.

Specifically, the pixel represented by the first symbol "○" is a pixel corresponding to the X-ray detection element that includes the semiconductor element 21a, the cathode 22a, and the anode 23a. The pixel represented by the second symbol "○" is a pixel corresponding to the X-ray detection element that includes the semiconductor element 21a, the cathode 22a, and the anode 24a. The pixel represented by the third symbol "○" is a pixel corresponding to the X-ray detection element that includes the semiconductor element 21b, the cathode 22b, and the anode 23b. The pixel represented by the fourth symbol "○" is a pixel corresponding to the X-ray detection element that includes the semiconductor element 21b, the cathode 22b, and the anode 24b.

The pixel represented by the fifth symbol "○" is a pixel corresponding to the X-ray detection element that includes the semiconductor element 21c, the cathode 22c, and the anode 23c. The pixel represented by the sixth symbol "○" is a pixel corresponding to the X-ray detection element that includes the semiconductor element 21c, the cathode 22c, and the anode 24c. The pixel represented by the seventh symbol "○" is a pixel corresponding to the X-ray detection element that includes the semiconductor element 21d, the cathode 22d, and the anode 23d. The pixel represented by the eighth symbol "○" is a pixel corresponding to the X-ray detection element that includes the semiconductor element 21d, the cathode 22d, and the anode 24d.

Here, the pixel corresponding to the X-ray detection element including the anode 23a located on the left side in FIG. 3 among the eight pixels represented by the symbols "○" will be described. If the X-ray detector module 12b including the semiconductor element 51a, the cathode 52a, and the anode 53a is not provided, the characteristics of the subject pixel may be degraded because of the same reason as described above in the comparative example.

However, in the first embodiment, the X-ray detector module 12b is arranged and generates an electric field, so that the characteristics of the pixel corresponding to the X-ray detection element including the anode 23a becomes equal to the characteristics of the six pixels located in other than the end portions in the slice direction among the eight pixels represented by the symbols "○". That is, the X-ray detector module 12b including the semiconductor element 51a, the cathode 52a, and the anode 53a generates an electric field such that the characteristics of the pixel corresponding to the X-ray detection element including the anode 23a becomes equal to the characteristics of the six pixels as described above. A magnitude of the bias voltage applied by the power source 60 and a magnitude of the bias voltage applied by the power source 55a are the same or substantially the same with each other in order to generate the electric field as described above.

The characteristics of the pixel corresponding to the X-ray detection element including the anode 24d becomes equal to the characteristics of the six pixels as described above because the X-ray detector module 12b including the semiconductor element 51b, the cathode 52b, and the anode 53b generates an electric field. Therefore, for example, a magnitude of the bias voltage applied by the power source 60 and a magnitude of the bias voltage applied by the power source 55b are the same or substantially the same with each other.

Meanwhile, the magnitude of the bias voltage applied by the power source 60 and the magnitudes of the bias voltage applied by the power sources 55a and 55b need not be the same, but may be different from each other. In this case, the characteristics of the pixel corresponding to the X-ray detection element including the anode 23a and the characteristics of the pixel corresponding to the X-ray detection element including the anode 24d are not completely the same. However, the characteristics of the pixel corresponding to the X-ray detection element including the anode 23a and the characteristics of the pixel corresponding to the X-ray detection element including the anode 24d are improved as compared to a case in which the X-ray detector module 12b is not provided.

Therefore, according to the X-ray detector 12 and the X-ray CT apparatus 1 of the first embodiment, it is possible to prevent degradation of the characteristics of the X-ray detection elements located in the end portions in the slice direction among the plurality of X-ray detection elements that contribute to generation of image data.

Thus, the first embodiment has been described. The X-ray detector 12 according to the first embodiment is an X-ray detector of the direct conversion type in which the plurality of X-ray detection elements are arranged in the column direction and the channel direction and voltage is applied between the anodes 23, 24, 53 and the cathodes 22, 52. Further, the ASIC 27 performs control so as not to read data from the X-ray detection elements in the end portions in the slice direction of the X-ray detection elements, and so as to read data from the X-ray detection elements in other than the end portions. That is, the ASIC 27 performs control so as not to use, for generation of image data, data from the X-ray detection elements in the end portions in the slice direction of the X-ray detection elements, and so as to use, for generation of image data, data from the X-ray detection elements in other than the end portions. Therefore, it is possible to prevent degradation of the characteristics of the X-ray detection elements located in the end portions in the slice direction among the plurality of X-ray detection elements that contribute to generation of image data. The ASIC 27 is one example of a control unit. Further, the ASIC 27 is one example of processing circuitry.

Furthermore, in the first embodiment, the same bias voltage is applied to the X-ray detection elements in the end portions and the X-ray detection elements in other than the end portions. Therefore, it is possible to match the characteristics of the X-ray detection elements in the end portions in the slice direction and the characteristics of the X-ray detection elements in other than the end portions among the plurality of X-ray detection elements that contribute to generation of image data.

Moreover, in the first embodiment, the X-ray detector 12 includes the plurality of X-ray detector modules 12a and 12b that include the plurality of X-ray detection elements and that are arranged in the slice direction and the channel direction in a two-dimensional manner. Furthermore, the X-ray detector modules 12b in the end portions in the slice direction among the plurality of X-ray detector modules 12a and 12b include the X-ray detection elements in the end portions. Moreover, the X-ray detector modules 12a other than the X-ray detector modules 12b in the end portions among the plurality of X-ray detector modules 12a and 12b include the X-ray detection elements in other than the end portions. The X-ray detector modules 12b need not be non-defective products, but may be remainder materials. Therefore, it is expected to improve yield of the X-ray detector 12.

Furthermore, the X-ray detector modules 12b are arranged in the end portions in the slice direction. Therefore, according to the first embodiment, it is possible to match a charge sharing amount between the X-ray detector module 12b and the X-ray detector module 12a that are adjacent to each other in the slice direction and a charge sharing amount between the two X-ray detector modules 12a that are adjacent to each other in the slice direction. Moreover, according to the first embodiment, the X-ray detector modules 12b are able to absorb scattered radiation.

Meanwhile, in the first embodiment, it may be possible to use members that generate the same electric field distributions as the electric field distributions generated by the X-ray detector modules 12b, instead of the X-ray detector modules 12b. Even with use of the members as described above, it is possible to achieve the same effects as those achieved with use of the X-ray detector modules 12b.

Furthermore, the X-ray detector modules 12a and the X-ray detector modules 12b may be configured with different materials or may be configured with the same material.

Second Embodiment

In the first embodiment, a case has been described in which the X-ray detector modules 12b as dummy X-ray detector modules are used, but it is not necessary to use the X-ray detector modules 12b. Therefore, embodiments for the above will be described as a second embodiment and a third embodiment. The second embodiment is first described, and thereafter, the third embodiment will be described. Meanwhile, in the description of the second embodiment, differences from the first embodiment will be mainly described, and explanation of the same configurations as those of the first embodiment may be omitted.

Figure 5:
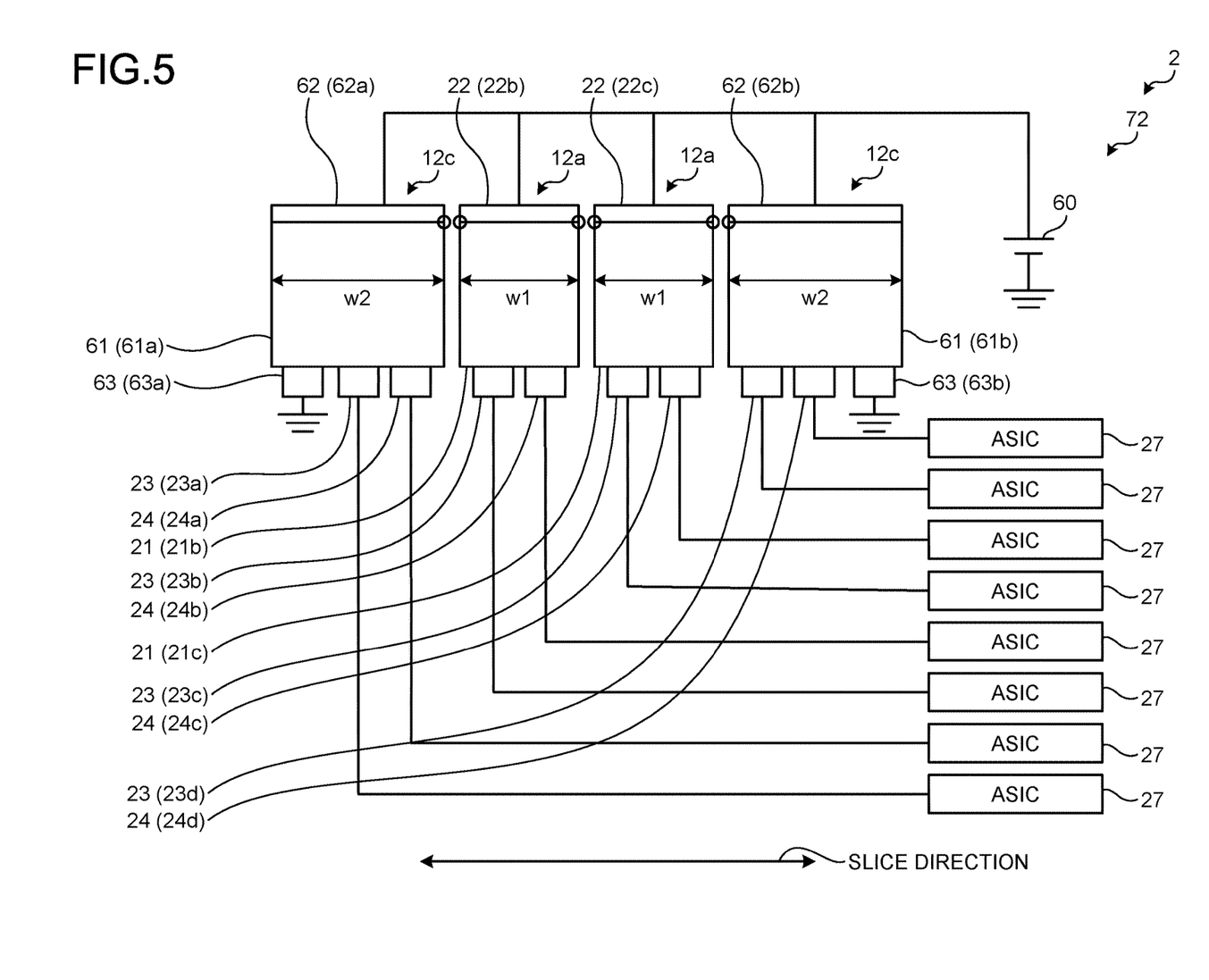
FIG. 5 is a diagram illustrating an example of a configuration of an X-ray detector of an X-ray CT apparatus according to a second embodiment.

FIG. 5 is a diagram illustrating an example of a configuration of an X-ray detector of the X-ray CT apparatus according to the second embodiment. An X-ray CT apparatus 2 according to the second embodiment is different from the X-ray CT apparatus 1 according to the first embodiment in that it includes an X-ray detector 72 as illustrated in FIG. 5, instead of the X-ray detector 12. Further, the X-ray detector 72 according to the second embodiment is different from the X-ray detector 12 according to the first embodiment in that it does not include the X-ray detector modules 12b. Furthermore, the X-ray detector 72 according to the second embodiment is different from the X-ray detector 12 in that it includes two X-ray detector modules 12c, instead of the two X-ray detector modules 12a. In the example in FIG. 5, the X-ray detector modules 12c are arranged in both end portions in the slice direction.

Each of the X-ray detector modules 12c includes a semiconductor element 61, a cathode 62, the anodes 23 and 24, and an anode 63. A dimension (width) "w2" of each of the X-ray detector modules 12c in the slice direction is larger than a dimension "w1" of each of the X-ray detector modules 12a in the slice direction. Therefore, in the X-ray detector modules 12c, the anode 63 is further arranged in addition to the anodes 23 and 24.

In the following description, when the two semiconductor elements 61 are explained in a distinguished manner, the two semiconductor elements 61 will be referred to as semiconductor elements 61a and 61b. Further, when the two cathodes 62 are explained in a distinguished manner, the two cathodes 62 will be referred to as cathodes 62a and 62b. Furthermore, when the two anodes 63 are explained in a distinguished manner, the two anodes 63 will be referred to as anodes 63a and 63b.

In the example in FIG. 5, in the single X-ray detector module 12c, a single X-ray detection element includes, for example, the semiconductor element 61, the cathode 62, and the anode 23. Further, the single X-ray detection element includes, for example, the semiconductor element 61, the cathode 62, and the anode 24. Furthermore, the single X-ray detection element includes, for example, the semiconductor element 61, the cathode 62, and the anode 63. A single X-ray detection element may correspond to a single pixel, or a plurality of X-ray detection elements may correspond to a single pixel. In the following description, a case will be descried in which the single X-ray detection element corresponds to the single pixel.

The cathode 62 is connected to the power source 60. The power source 60 applies bias voltage to the X-ray detector module 12c. More specifically, the power source 60 applies bias voltage between the cathode 62 and the anodes 23, 24, 63. By applying the bias voltage to the X-ray detection element, the X-ray detection element enters a certain state in which it is possible to output a 1-pulse electrical signal at every incidence of an X-ray photon.

Here, the anode 63 is grounded and an ASIC that is a read circuit is not connected to the anode 63. Therefore, a signal from the anode 63 is not used for generation of image data. For example, in the second embodiment, with application of the bias voltage, the X-ray detection element including the anode 63a generates an electric field and prevents degradation of characteristics of the X-ray detection element including the anode 23a. Further, with application of the bias voltage, the X-ray detection element including the anode 63b generates an electric field and prevents degradation of characteristics of the X-ray detection element including the anode 24d.

Therefore, according to the X-ray detector 72 and the X-ray CT apparatus 2 of the second embodiment, it is possible to prevent degradation of the characteristics of the X-ray detection elements in the end portions in the slice direction among the plurality of X-ray detection elements that contribute to generation of image data.

Thus, the second embodiment has been described above. The X-ray detector 72 according to the second embodiment includes the plurality of X-ray detectors modules 12a and 12c that include the plurality of X-ray detection elements and that are arranged in the slice direction and the channel direction. Further, the X-ray detector modules 12c located in the end portions in the slice direction among the plurality of X-ray detector modules 12a and 12c include the X-ray detection elements (the X-ray detection elements including the anodes 63). Furthermore, the X-ray detector modules 12c include some X-ray detection elements among the X-ray detection elements in other than the end portions. Examples of the some X-ray detection elements among the X-ray detection elements in other than the end portions include the X-ray detection element including the anode 23a, the X-ray detection element including the anode 24a, the X-ray detection element including the anode 23d, and the X-ray detection element including the anode 24d. Moreover, the X-ray detector modules 12a other than the X-ray detector modules 12c in the end portions include the X-ray detection elements except for the some X-ray detection elements among the X-ray detection elements in other than the end portions. That is, the X-ray detector modules 12a include the X-ray detection element including the anode 23b, the X-ray detection element including the anode 24b, the X-ray detection element including the anode 23c, and the X-ray detection element including the anode 24c. With this configuration, as described above, it is possible to prevent degradation of the characteristics of the X-ray detection elements in the end portions in the slice direction among the plurality of X-ray detection elements that contribute to generation of image data.

Third Embodiment

A third embodiment will be described below. Meanwhile, in explanation of the third embodiment, differences from the first embodiment will be mainly described, and explanation of the same configurations as those of the first embodiment may be omitted.

Figure 6:
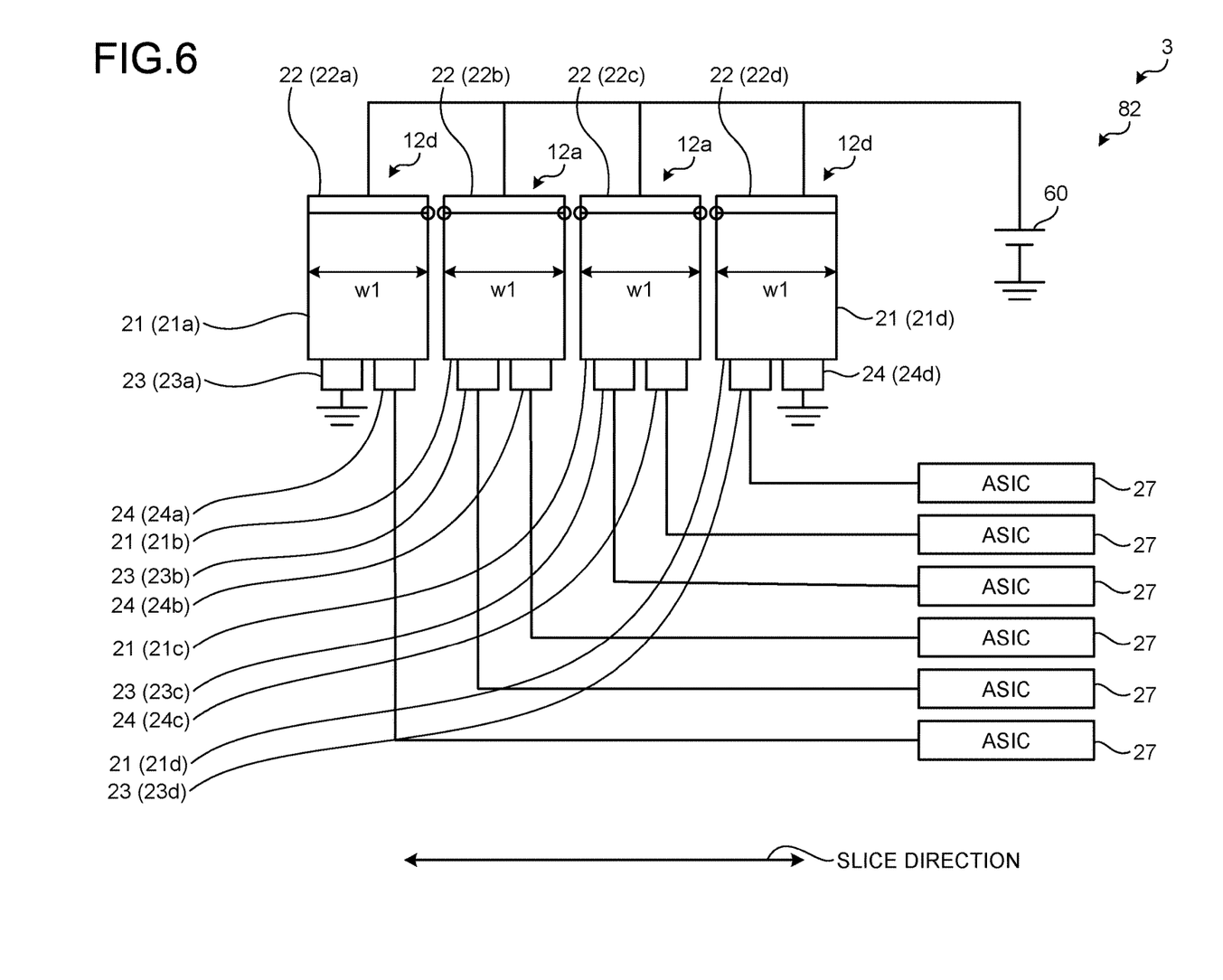
FIG. 6 is a diagram illustrating an example of a configuration of an X-ray detector of an X-ray CT apparatus according to a third embodiment.

FIG. 6 is a diagram illustrating an example of a configuration of an X-ray detector of an X-ray CT apparatus according to the third embodiment. An X-ray CT apparatus 3 according to the third embodiment is different from the X-ray CT apparatus 1 according to the first embodiment in that it includes an X-ray detector 82 as illustrated in FIG. 6, instead of the X-ray detector 12. Further, the X-ray detector 82 according to the third embodiment is different from the X-ray detector 12 according to the first embodiment in that it does not include the X-ray detector modules 12b. Furthermore, the X-ray detector 82 according to the third embodiment is different from the X-ray detector 12 in that it includes two X-ray detector modules 12d, instead of the two X-ray detector modules 12a. In the example in FIG. 6, the X-ray detector modules 12d are arranged in both end portions in the slice direction.

The X-ray detector module 12d includes the semiconductor element 21, the cathode 22, and the anodes 23 and 24. A dimension "w1" of each of the X-ray detector modules 12d in the slice direction is the same as a dimensions "w1" of each of the X-ray detector modules 12a in the slice direction.

In the third embodiment, the anodes 23a and 24d are grounded and ASICs that are read circuits are not connected to the anodes 23a and 24d. Therefore, a signal from the anodes 23a and 24d is not used for generation of image data. For example, in the third embodiment, with application of bias voltage, the X-ray detection element including the anode 23a generates an electric field and prevents degradation of characteristics of the X-ray detection element including the anode 24a. Further, with application of bias voltage, the X-ray detection element including the anode 24d generates an electric field and prevents degradation of characteristics of the X-ray detection element including the anode 23d.

Therefore, according to the X-ray detector 82 and the X-ray CT apparatus 3 of the third embodiment, it is possible to prevent degradation of the characteristics of the X-ray detection elements in the end portions in the slice direction among the plurality of X-ray detection elements that contribute to generation of image data.

Thus, the third embodiment has been described above. According to the third embodiment, as described above, it is possible to prevent degradation of the characteristics of the X-ray detection elements in the end portions in the slice direction among the plurality of X-ray detection elements that contribute to generation of image data.

Meanwhile, in the first embodiment, the second embodiment, and the third embodiment, it may be possible to connect the ASICs 27 to the X-ray detection elements in the end portions in the slice direction, and cause the ASICs 27 to read signals (data) output by the X-ray detection elements in the end portions, perform a process on the read signals, and output the signals to the DAS 18. Meanwhile, the signals as described above may be used for scattered radiation correction and dark count correction performed by the preprocessing function 442. However, the signals as described above are not used for generation of image data. That is, the ASICs 27 perform control so as not to use, for generation of image data, the read signals output from the X-ray detection elements in the end portions.

Figure 7:
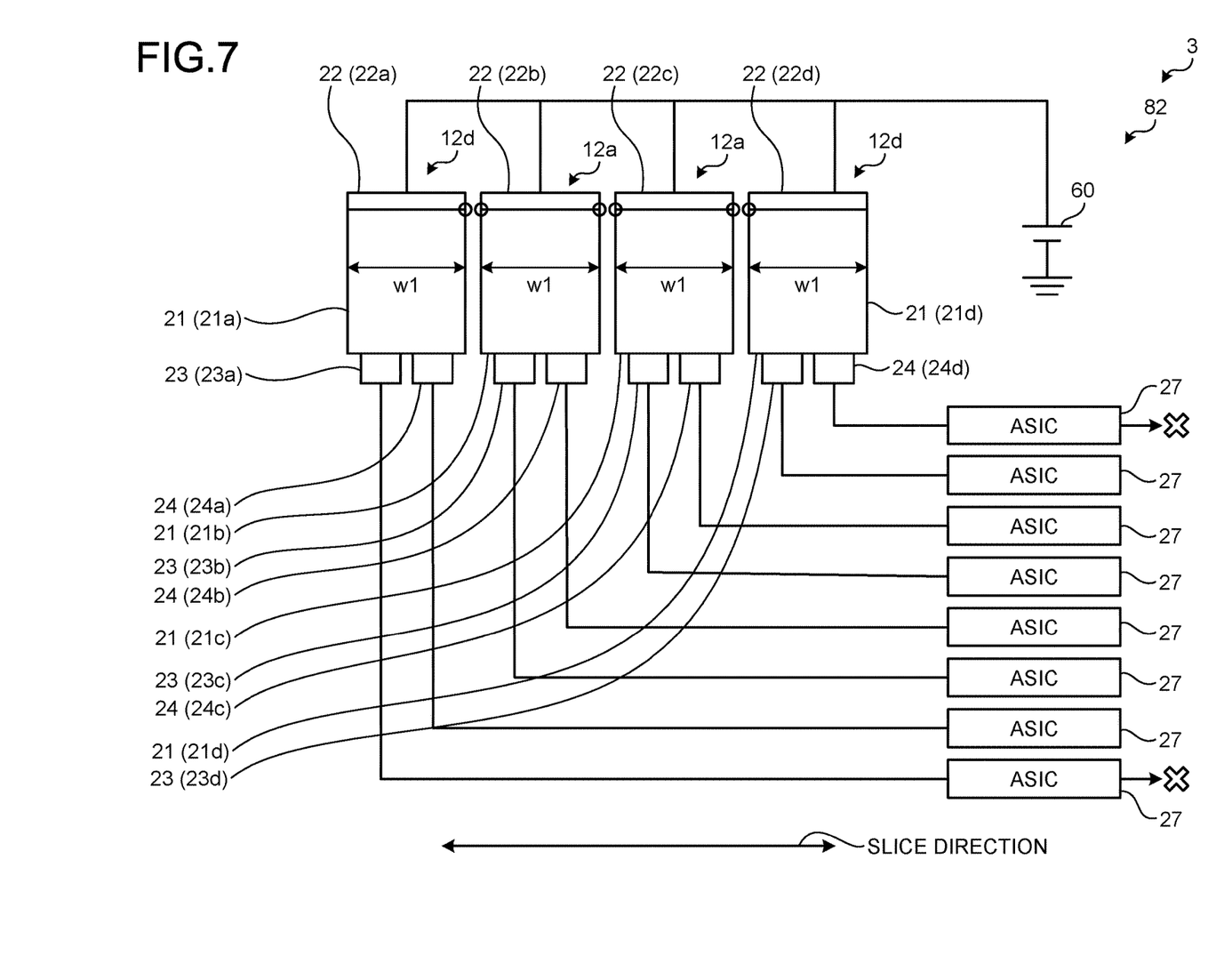
FIG. 7 is a diagram illustrating an example of a configuration of an X-ray detector of an X-ray CT apparatus according to a modification of the third embodiment.

FIG. 7 is a diagram illustrating an example of a configuration of an X-ray detector of an X-ray CT apparatus according to a modification of the third embodiment. For example, as illustrated in FIG. 7, the ASIC 27 may be connected to the anode 23a and the ASIC 27 may be connected to the anode 24d. Further, the ASICs 27 may read signals output by the anodes 23a and 24d, perform a process on the read signals, and output the signals to the DAS 18. As described above, the signals as described above may be used for scattered radiation correction and dark count correction performed by the preprocessing function 442. However, the signals as described above are not used for generation of image data. That is, the ASIC 27 performs control so as not to use, for generation of image data, the read signals output from the anodes 23a and 24d.

Similarly, in the first embodiment, it may be possible to connect the ASICs 27 to the X-ray detector modules 12b and cause the ASICs 27 to read signals output from the X-ray detector modules 12b, perform a process on the read signals, and output the signals to the DAS 18. Further, in the second embodiment, the ASICs 27 may be connected to the anodes 63. Furthermore, the ASICs 27 may read signals output from the anodes 63, perform a process on the signals, and output the signals to the DAS 18.

Figure 8:
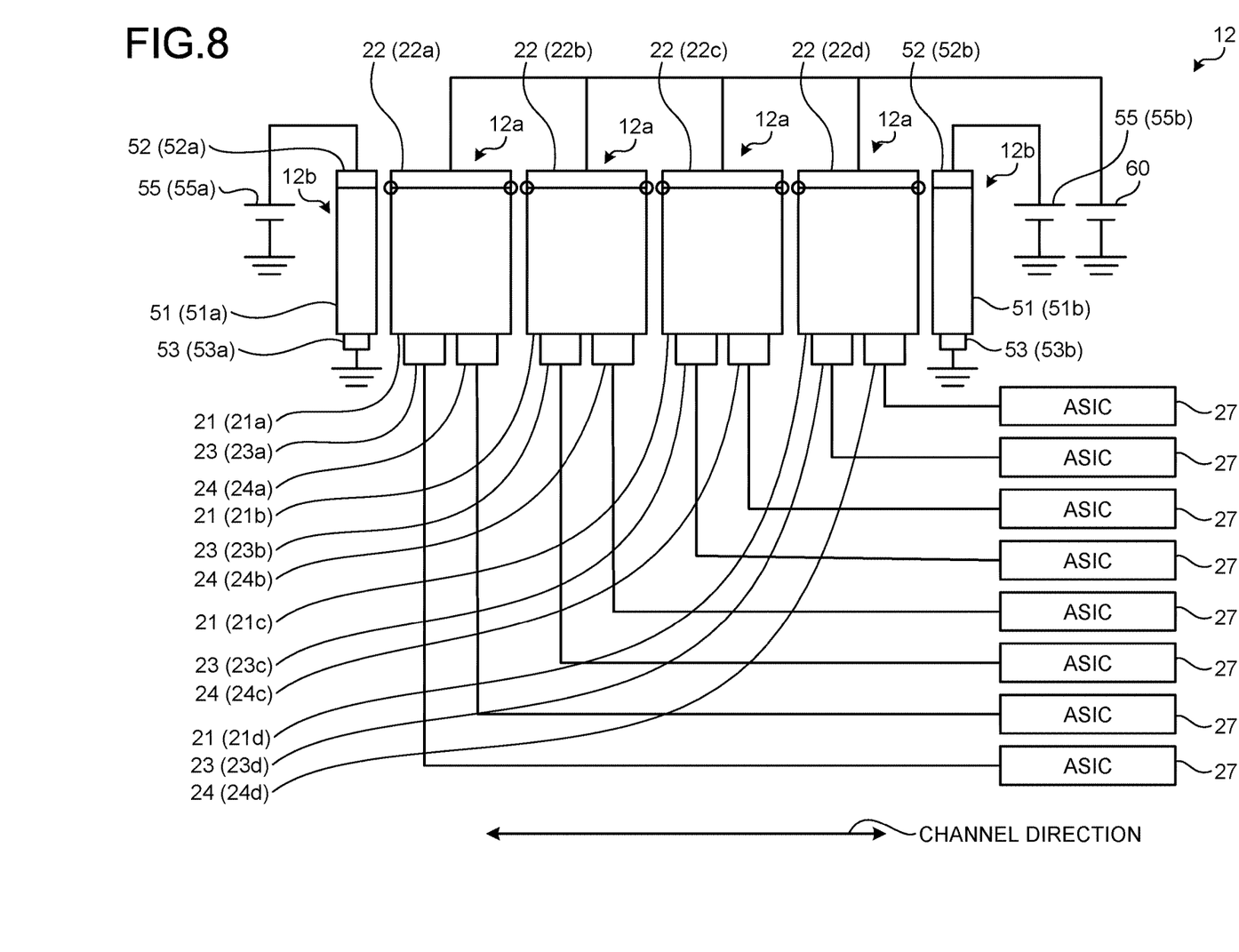
FIG. 8 is a diagram illustrating an example in which an X-ray detector 12 of the first embodiment is configured by replacing a "slice direction" with a "channel direction".

Furthermore, in the first embodiment, the second embodiment, and the third embodiment, the X-ray detectors 12, 72, and 82 may be configured such that the "slice direction" and the "channel direction" are appropriately replaced with each other. With this configuration, it is possible to prevent degradation of the X-ray detection elements located in the end portions in the channel direction among a plurality of X-ray detection elements that contribute to generation of image data. FIG. 8 is a diagram illustrating an example of a case in which the X-ray detector 12 of the first embodiment is configured by replacing the "slice direction" with the "channel direction". As illustrated in FIG. 8, for example, in the first embodiment, the plurality of X-ray detector modules 12b may be arranged in both end portions in the channel direction, along the slice direction. Further, a plurality of columns, each of which includes the plurality of X-ray detector modules 12a that are arranged along the slice direction, may be arranged along the channel direction between the X-ray detector modules 12b that are arranged in one end portion and the X-ray detector modules 12b that are arranged in the other end portion. In this manner, the X-ray detector 12 may include the plurality of X-ray detector modules 12a and 12b that include the plurality of X-ray detection elements and that are arranged in the slice direction and the channel direction in a two-dimensional manner. In this case, the ASICs 27 perform control so as not to red data from the X-ray detection elements located in the end portions in the channel direction of the X-ray detection elements, and so as to read data from the X-ray detection elements in other than the end portions. That is, the ASICs 27 perform control so as not to use, for generation of image data, data from the X-ray detection elements in the end portions in the channel direction of the X-ray detection element, and so as to use, for generation of image data, data from the X-ray detection elements in other than the end portions. Therefore, it is possible to prevent degradation of the characteristics of the X-ray detection elements in the end portions in the channel direction among the plurality of X-ray detection elements that contribute to generation of image data. Similarly to the case in which the X-ray detector 12 of the first embodiment is configured by replacing the "slice direction" and the "channel direction" with each other as illustrated in FIG. 8, it may be possible to configure the X-ray detectors 12, 72, and 82 of the second embodiments and the third embodiments by replacing the "slice direction" with the "channel direction".

The components of the apparatuses illustrated in the drawings are conceptual function, and need not be physically configured in the manner illustrated in the drawings. In other words, specific forms of distribution and integration of the apparatuses are not limited to those illustrated in the drawings, and all or part of the apparatuses may be functionally or physically distributed or integrated in arbitrary units depending on various loads or use conditions Further, all or an arbitrary part of the processing functions implemented by the apparatuses may be realized by a CPU and a program analyzed and executed by the CPU, or may be realized by hardware using wired logic.

Meanwhile, a phrase "processor" used in the description above indicates a circuitry, such as a central processing unit (CPU), a graphics processing unit (GPU), an application specific integrated circuit (ASIC), or a programmable logic device (for example, a simple programmable logic device (SPLD), a complex programmable logic device (CPLD), and a field programmable gate array (FPGA)). The processor implements functions by reading and executing a program stored in the memory 41. Meanwhile, the program may be directly incorporated in a circuit of the processor, instead of being stored in the memory 41. In this case, the processor implements functions by reading and executing the program incorporated in the circuit. Meanwhile, each of the processors in the embodiments need not be configured as a single circuit, but may be configured as a single processor by a combination of a plurality of independent circuits to implement functions. Further, a plurality of structural elements illustrated in each of the drawings may be integrated into a single processor to implement functions.

Here, the method explained in the embodiments as described above may be implemented by causing a computer, such as a personal computer or a workstation, to execute a program that is prepared in advance. The program is provided by being incorporated in a read only memory (ROM), a memory, or the like in advance. Meanwhile, the program may be provided by being stored in a computer-readable storage medium, such as a compact disk (CD)-ROM, a flexible disk (FD), a CD-recordable (R), or a digital versatile disk, in a computer installable or a computer executable file format. Furthermore, the program may be stored in a computer connected to a network, such as the Internet, and may be provided or distributed by download via the network. For example, the program may be configured with a module including each of functional units. As actual hardware, CPU reads the program from a storage medium, such as a ROM, and executes the program, so that each of the modules is loaded on a main storage device and generated on the main storage device.

According to at least one embodiment as described above, it is possible to prevent degradation of characteristics of X-ray detection elements in end portions in the slice direction or the channel direction among a plurality of X-ray detection elements that contribute to generation of image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray detector of a direct conversion type in which a plurality of X-ray detection elements are arranged in a column direction and a channel direction and voltage is applied between anodes and cathodes, the X-ray detector comprising:
   processing circuitry configured to perform control so as not to use, for generation of image data, data from the X-ray detection elements in end portions in one of the column direction and the channel direction of the X-ray detection elements, and so as to use, for generation of image data, data from the X-ray detection elements in other than the end portions,
   wherein the processing circuitry is further configured to perform control so as to read data from the X-ray detection elements in the end portions and data from the X-ray detection elements in other than the end portions, and prevent the data read from the X-ray detection elements in the end portions from being used for the generation of the image data.

2. The X-ray detector according to claim 1, wherein a substantially identical voltage is applied to the X-ray detection elements in the end portions and the X-ray detection elements in other than the end portions.

3. The X-ray detector according to claim 1, further comprising:
   a plurality of X-ray detector modules that include the plurality of X-ray detection elements and that are arranged in one of the column direction and the channel direction, wherein
   the X-ray detector modules in end portions in one of the column direction and the channel direction among the plurality of X-ray detector modules include the X-ray detector elements in the end portions, and
   the X-ray detector modules other than the X-ray detector modules in the end portions include the X-ray detection elements in other than the end portions.

4. The X-ray detector according to claim 3, wherein the X-ray detector modules in the end portions and the X-ray detector modules other than the X-ray detector modules in the end portions are made with different materials.

5. The X-ray detector according to claim 1, further comprising:
   a plurality of X-ray detector modules that include the plurality of X-ray detection elements and that are arranged in one of the column direction and the channel direction, wherein
   the X-ray detector modules in end portions in one of the column direction and the channel direction among the plurality of X-ray detector modules include the X-ray detection elements in the end portions and some of the X-ray detection elements in other than the end portions.

6. The X-ray detector according to claim 5, wherein a dimension of each of the X-ray detector modules in the end portions in one of the column direction and the channel direction is larger than a dimension of each of the X-ray detector modules other than the X-ray detector modules in the end portions in one of the column direction and the channel direction.

7. The X-ray detector according to claim 5, wherein a dimension of each of the X-ray detector modules in the end portions in one of the column direction and the channel direction is identical to a dimension of each of the X-ray detector modules other than the X-ray detector modules in the end portions in one of the column direction and the channel direction.

8. An X-ray detector of a direct conversion type in which a plurality of X-ray detection elements are arranged in a column direction and a channel direction and voltage is applied between anodes and cathodes, the X-ray detector comprising:
   processing circuitry configured to use, for generation of first image data, data from the X-ray detection elements in other than end portions in one of the column direction and the channel direction of the X-ray detection elements, and use, for correction of first image data, data from the X-ray detection elements in the end portions.

9. The X-ray detector according to claim 8, wherein the processing circuitry is further configured to perform scattered radiation correction or dark count correction on the first image data.

* * * * *